US012612377B2

(12) United States Patent
Pazenok et al.

(10) Patent No.: US 12,612,377 B2
(45) Date of Patent: Apr. 28, 2026

(54) PROCESS FOR PREPARING AMINOFURANES

(71) Applicant: Bayer Aktiengesellschaft, Leverkusen (DE)

(72) Inventors: Sergii Pazenok, Leichlingen (DE); Winfried Etzel, Leichlingen (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 355 days.

(21) Appl. No.: 18/006,068

(22) PCT Filed: Jul. 20, 2021

(86) PCT No.: PCT/EP2021/070212
§ 371 (c)(1),
(2) Date: Jan. 19, 2023

(87) PCT Pub. No.: WO2022/018057
PCT Pub. Date: Jan. 27, 2022

(65) Prior Publication Data

US 2023/0339876 A1 Oct. 26, 2023

(30) Foreign Application Priority Data

Jul. 23, 2020 (EP) .................................... 20187433

(51) Int. Cl.
*C07D 307/70* (2006.01)
*C07D 307/68* (2006.01)

(52) U.S. Cl.
CPC .................................. *C07D 307/70* (2013.01)

(58) Field of Classification Search
None
See application file for complete search history.

(56) References Cited

U.S. PATENT DOCUMENTS

| | | | |
|---|---|---|---|
| 8,586,753 | B2 | 11/2013 | Pazenok et al. |
| 9,078,442 | B2 | 7/2015 | Willms |
| 9,516,880 | B2 | 12/2016 | Haaf et al. |
| 9,585,392 | B2 | 3/2017 | Kuhn |
| 10,104,892 | B2 | 10/2018 | Frenzel et al. |
| 11,597,724 | B2 | 3/2023 | Peters et al. |
| 11,613,522 | B2 | 3/2023 | Peters et al. |
| 12,171,230 | B2 | 12/2024 | Trabold et al. |
| 12,185,723 | B2 | 1/2025 | Van Almsick |
| 12,319,664 | B2 | 6/2025 | Bojack et al. |
| 2021/0292312 | A1 | 9/2021 | Peters et al. |
| 2022/0053762 | A1 | 2/2022 | Trabold |
| 2022/0386605 | A1 | 12/2022 | Lorentz et al. |
| 2023/0104990 | A1 | 4/2023 | Olenik |
| 2023/0189808 | A1 | 6/2023 | Dittgen et al. |
| 2023/0200390 | A1 | 6/2023 | Dittgen et al. |
| 2023/0200393 | A1 | 6/2023 | Dittgen et al. |
| 2023/0200394 | A1 | 6/2023 | Dittgen et al. |
| 2023/0217926 | A1 | 7/2023 | Dittgen et al. |
| 2023/0240297 | A1 | 8/2023 | Dittgen et al. |
| 2023/0265062 | A1 | 8/2023 | Hoemberger et al. |
| 2023/0276792 | A1 | 9/2023 | Dittgen et al. |
| 2023/0348366 | A1 | 11/2023 | Rembiak |
| 2025/0042863 | A1 | 2/2025 | Cibu et al. |
| 2025/0057164 | A1 | 2/2025 | Lorentz et al. |
| 2025/0122158 | A1 | 4/2025 | Lishchynskyi et al. |

FOREIGN PATENT DOCUMENTS

| | | | |
|---|---|---|---|
| WO | 2011/073101 | A1 | 6/2011 |
| WO | 2011073100 | A1 | 6/2011 |
| WO | 2014048940 | A2 | 4/2014 |
| WO | 2018/228985 | A1 | 12/2018 |
| WO | 2019034602 | A1 | 2/2019 |

OTHER PUBLICATIONS

Igor et al. Eur. J. Org. Chem. 2018, 3853-3861.*
International Search Report of International Patent Application No. PCT/EP2021/070212, mailed Sep. 30, 2021.
Gerus et al., "Synthesis and Properties of Polyfunctional Cyclic [beta]-Alkoxy-[alpha], [beta]-Unsaturated Ketones Based on 4-Methylene-I,3-dioxolanes" , European Journal of Organic Chemistry, 2018, pp. 3853-3861.
Woods et al., "Synthesis and DNA Binding Properties of Saturated Distamycin Analogues", Bioorganic & Medicinal Chemistry Letters, 2002, pp. 2647-2650, vol. 12, No. 18.
Brucoli et al., "Efficient synthesis and biological evaluation of proximicins A, B and C", Bioorganic & Medicinal Chemistry, Elsevier, 2012,pp. 2019-2024, vol. 20.
Wolter et al., "Total Synthesis of Proximicin A-C and Synthesis of New Furan-Based DNA Binding Agents", Organic Letters, 2009, pp. 2804-2807, vol. 11, No. 13.
Wang et al: "Base-Mediated Tunable Synthesis of 2-Trifluoromethylated Furans and Dihydrofuranols: Extraordinary Stable in Sulfuric Acid", Journal of Organic Chemistry, Bd. 84, Nr. 23, 7. Nov. 2019.

* cited by examiner

*Primary Examiner* — Sun Jae Yoo
(74) *Attorney, Agent, or Firm* — Paul D. Tietz; Michael Vanengelen

(57) ABSTRACT

The present invention relates to a novel method for preparing 4-aminofurans of the general formula (I) and salts thereof.

19 Claims, No Drawings

PROCESS FOR PREPARING AMINOFURANES

CROSS-REFERENCE TO RELATED APPLICATIONS

This application is the National Stage entry of International Application No. PCT/EP2021/070212, filed 20 Jul. 2021, which claims priority to European Patent Application No. 20187433.6, filed 23 Jul. 2020.

BACKGROUND

Field

The present invention relates to a novel method for preparing 4-aminofurans of the general formula (I) and salts thereof.

Description of Related Art

4-Aminofurans of the general formula (I) (especially $R^1$=COOMe) are important precursors of agrochemical active ingredients (cf. WO2018/228985) and pharmaceutical active ingredients (e.g. DNA binding agents: Woods, Craig R. et al. Bioorganic & Medicinal Chemistry Letters, 12(18), 2647-2650; 2002).

4-Aminofurans of the general formula (I) serve as starting material for the preparation of tetrahydro- and dihydrofurancarboxylic acids and esters. To date, these compounds of the formula (I) have been prepared by a multi-stage synthesis including a bromination, dehalogenation, coupling reaction and deprotection. (see F. Brucoli, et al. Bioorganic & Medicinal Chemistry, 20(6), 2019-2024; 2012).

Scheme 1

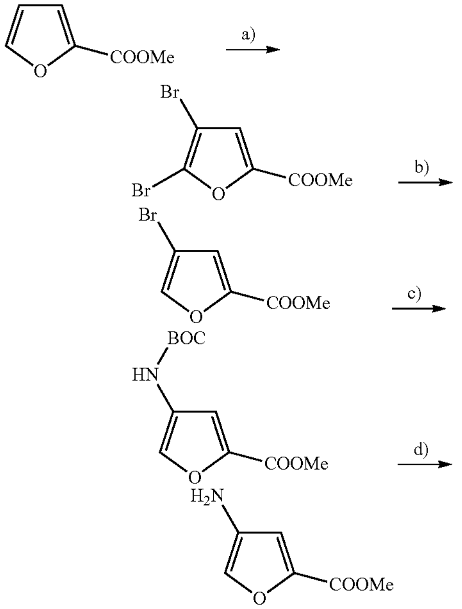

a) $Br_2$, $AlCl_3$; b) Zn, $NH_4Cl$; c) CuI/$(CH_3NHCH_2)_2$, Boc—$NH_2$, $K_2CO_3$ d) removal of Boc protecting group The synthesis mentioned above has a large number of disadvantages, such as low atom economy (bromination and dehalogenation), use of heavy metals such as zinc and use of protecting groups such as Boc-amine. The method described in Bioorganic & Medicinal Chemistry, 20(6), 2019-2024; 2012 furthermore requires the use of metal-containing (for example copper(I) iodide) catalysts.

These disadvantages render the method for preparing compounds of the general formula (I) uneconomic and therefore very expensive.

F. Wolter et al in (Organic Letters, 11(13), 2804-2807; 2009) describes another method for preparing aminofurans of the general formula (I), specifically via a Curtius rearrangement of dimethyl furan-2,4-dicarboxylate using $(PhO_3)_2P(O)N_3$. This method is unsuitable for industrial applications due to the highly explosive properties of organic azides.

Several compounds of the general formula (I), for example where $R^1$=$CF_3$ and $R^2$=NHAryl, have been described in European Journal of Organic Chemistry 2018, 3853-3861. However, this compound was detected in a mixture of several components.

SUMMARY

In light of the prior art described above, the object of the present invention is to find a method for preparing the compounds specified, which is cost-effective and which can be used on an industrial scale. It is also desirable to obtain these compounds with high yield and at high purity, such that they do not have to be subjected to any further complex purification.

The object described above—simple, cost-effective and large-scale production—is achieved by a method for preparing compounds of the general formula (I) and salts thereof

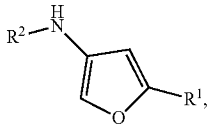

(I)

in which $R^1$ is $CF_3$, $CF_2H$, $C_2F_5$, $CF_2Cl$, $CCl_3$, $COO(C_1\text{-}C_4)$alkyl, COOH, $R^2$ is H, $CH_3CO$, $CCl_3CO$, $CF_3CO$, phenyl-CO, $CH_3OCO$, $(CH_3)_3COCO$, phenyl, phenyl-$CH_2$, (diphenyl)CH, characterized in that in a first step compounds of the general formula (II)

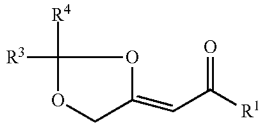

(II)

in which $R^3$ and $R^4$ are each independently H and $C_1$-$C_4$-alkyl and $R^1$ has the definitions specified above, with the aid of an amine of the general formula $R^5$—$NH_2$ (V) are converted to compounds of the general formula (III)

(III)

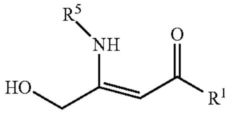

in which $R^5$ is H, phenyl, phenyl-$CH_2$, (diphenyl)CH, and in a second reaction step these are then reacted in the presence of a dehydrating reagent to give compounds of the general formula (I).

DETAILED DESCRIPTION OF A PREFERRED EMBODIMENT

Preferred definitions of the radicals of the compounds of the general formulae (I), (II), (III), (IV) and (V) are as follows:

is $CF_3$, $CF_2H$, $CF_2Cl$, $C_2F_5$, $CCl_3$, $COOCH_3$, $COOC_2H_5$, $R^2$ is H, $CF_3CO$, $CH_3CO$, $CCl_3CO$, phenyl, phenyl-$CH_2$, (diphenyl)CH, $CH_3OCO$, $(CH_3)_3COCO$, $R^3$ and $R^4$ are each independently H or $CH_3$, $R^5$ is H, phenyl, phenyl-$CH_2$, (diphenyl)CH.

Particularly preferred definitions of the radicals of the compounds of the general formulae (I), (II), (III), (IV) and (V) are as follows:

$R^1$ is $CF_3$, $CF_2H$, $CCl_3$, $COOCH_3$, $COOC_2H_5$, $R^2$ is H, $COCF_3$, $COCH_3$, $COCCl_3$, Ph-$CH_2$, (diphenyl) CH, $CH_3OCO$, $(CH_3)_3COCO$, $R^3$ and $R^4$ are each independently H or $CH_3$, $R^5$ is H.

Especially preferred definitions of the radicals of the compounds of the general formulae (I), (II), (III), (IV) and (V) are as follows:

$R^1$ is $CF_3$, $COOCH_3$, $COOC_2H_5$, $R^2$ is H, $COCF_3$, $(CH_3)_3COCO$, $R^3$ and $R^4$ are $CH_3$, $R^5$ is H.

Further especially preferred definitions of the radicals of the compounds of the general formulae (I), (II), (III), (IV) and (V) are as follows:

$R^1$ is $COOCH_3$, $COOC_2H_5$, $R^2$ is H, $R^3$ and $R^4$ are $CH_3$, $R^5$ is H.

Further especially preferred definitions of the radicals of the compounds of the general formulae (I), (II), (III), (IV) and (V) are as follows:

$R^1$ is $COOCH_3$, $R^2$ is H, $R^3$ and $R^4$ are $CH_3$, $R^5$ is H.

The reaction sequence for preparing compounds of the formula (I) is shown in Scheme 2:

Scheme 2

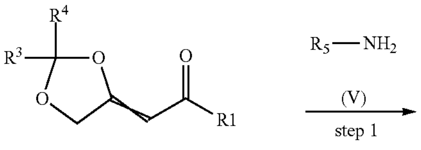

(II)

-continued

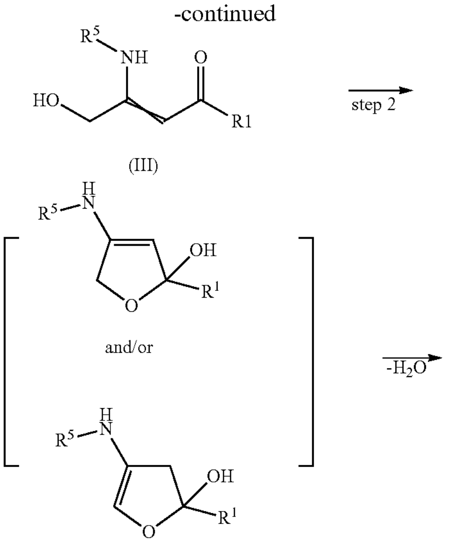

(III)

(IV)

(I)

The compounds of the formula (II) react in the first reaction step with ammonia or amines (compounds of the general formula (V)) to form compounds of the general formula (III), which are then converted in the second reaction step to compounds of the general formula (I). Several compounds of the general formula (II) and (III), in which $R^1$, $R^3$, $R^4$ and $R^5$ have the definitions specified above, are known. These compounds can be prepared by the method known from WO 2011/073100, WO 2011/073101 and European Journal of Organic Chemistry (2018), 2018(27-28), 3853-3861.

By way of example, the following compounds of the formula (II) may be mentioned:

(II)

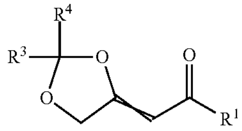

3-(2,2-dimethyl-1,3-dioxolan-4-ylidene)-1,1,1-trifluoropropan-2-one 3-(1,3-dioxolan-4-ylidene)-1,1,1-trifluoropropan-2-one methyl 3-(2,2-dimethyl-1,3-dioxolan-4-ylidene)-2-oxopropanoate ethyl 3-(2,2-dimethyl-1,3-dioxolan-4-ylidene)-2-oxopropanoate By way of example, the following compounds of the formula (III) may be mentioned:

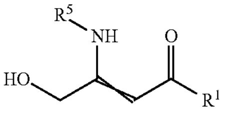

(III)

4-amino-1,1,1-trifluoro-5-hydroxypent-3-en-2-one
4-amino-1,1-difluoro-5-hydroxypent-3-en-2-one
4-amino-1,1,1-trichloro-5-hydroxypent-3-en-2-one
methyl 4-amino-5-hydroxy-2-oxopent-3-enoate
ethyl 4-amino-5-hydroxy-2-oxopent-3-enoate
methyl 4-benzylamino-5-hydroxy-2-oxopent-3-enoate.

In the second reaction step, the compounds of the formula (III) are cyclized. The ring closure takes place in the presence of a dehydrating reagent such as $SOCl_2$, $POCl_3$, $PCl_3$, phosgene, diphosgene, triphosgene, ClCOCOCl, $(CF_3CO)_2$, $P_4O_{10}$, $SO_2F_2$, trimethyl orthoformate and triethyl orthoformate and HCl. Preferred dehydrating reagents are $SOCl_2$, $POCl_3$, $PCl_3$, phosgene, diphosgene, triphosgene and ClCOCOCl. Especially preferred dehydrating reagents are $SOCl_2$, $POCl_3$, ClCOCOCl and phosgene.

Using reagents such as $SOCl_2$, $POCl_3$, $PCl_3$, phosgene, diphosgene, triphosgene and ClCOCOCl, compounds of the formula (I) where $R^2$=H, $CH_3$, phenyl, phenyl-$CH_2$ and (diphenyl)CH are obtained. Said compounds are formed in the form of HCl salts thereof.

If the compounds of the general formula (I) are obtained in the form of salts thereof, for example as a hydrochloride, the salt-free forms can be obtained by treating the salt with a base, for example triethylamine (see Example 2).

Using reagents such as $(CF_3CO)_2O$, compounds of the formula (I) where $R^2$=$CF_3CO$ are obtained.

The molar ratio of the compound of the formula (III) to the cyclization reagents is in the range of about 1:0.1 to 1:5, preferably from 1:0.5 to 1:3.

Reaction step 2 is usually carried out in a temperature range of 0° C. to 40° C. and optionally in the presence of a solvent or diluent. The reaction is preferably carried out in a solvent at approximately room temperature (RT).

Preferred solvents are methanol, ethanol, isopropanol, butanol, acetonitrile, N,N-dimethylacetamide, toluene, chlorobenzene.

Description of the Methods and Intermediates

EXAMPLES

The present invention is elucidated in more detail by the examples which follow, without restricting the invention to these examples.

Method of Measurement

The products were characterized by $^1$H NMR spectroscopy and/or LC-MS (Liquid Chromatography Mass Spectrometry).

The NMR spectra were determined using a Bruker Avance 400 fitted with a flow probe head (volume 60 μl). In individual cases, the NMR spectra were measured with a Bruker Avance II 600.

Example 1

Methyl 4-aminofuran-2-carboxylate hydrochloride (salt of the formula (I)

15.9 g (0.1 mol) of methyl 4-amino-5-hydroxy-2-oxopent-3-enoate were suspended in 50 ml of methanol and the mixture was cooled to 0° C. 17.7 g (0.15 mol) of $SOCl_2$ were added thereto at 0° C. over 2 hours. The mixture was stirred at 10° C. for a further 5 hours and the precipitate was filtered off, washed with 5 ml of methanol and dried. This gave 16.8 g, 95% of pale beige crystals.

$^1$H-NMR (400 MHz, $CDCl_3$): δ 10.07 (3H, s, br.); 8.10 (1H, d); 7.32 (1H, d); 3.83 (3H, s) ppm.

$^{13}$C-NMR 158.0 (s); 143.6 (s); 140.2 (d); 121.8 (s); 114.5 (d); 52.3 (q) ppm.

Example 2

Conversion of methyl 4-aminofuran-2-carboxylate hydrochloride (salt of the formula (I)) to methyl 4-aminofuran-2-carboxylate (salt-free product of the formula (I))

9.2 g of methyl 4-aminofuran-2-carboxylate hydrochloride were suspended in 50 ml of ethyl acetate and 15.7 g of $Et_3N$ were added. The mixture was stirred at RT for 3 hours, the precipitate was filtered off and ethyl acetate fully concentrated under vacuum. This gave 6.96 g, 95% of beige crystals, with m.p. 79-81° C.

$^1$H-NMR (400 MHz, $CDCl_3$): δ: 7.24 (1H, d); 6.8 (1H, d); 4.3 (2H, s) 3.75 (3H, s) ppm.

Example 3

Methyl 4-[(2,2,2-trifluoroacetyl)amino]furan-2-carboxylate 1.59 g (0.01 mol) of methyl 4-amino-5-hydroxy-2-oxopent-3-enoate were suspended in 50 ml of dichloromethane and the mixture was cooled to 0° C. 2 ml of $(CF_3CO)_2O$ were added thereto at 0° C. over 2 hours. The mixture was stirred at 10° C. for a further 5 hours and 20 ml of water were added. The mixture was stirred for 5 h at room temperature (RT) and then the phases were separated. The organic phase was concentrated. The precipitate was stirred with 5 ml of diisopropyl ether and filtered off. This gave 1 mg of the product as a beige solid.

$^1$H-NMR (400 MHz, $CDCl_3$): δ 11.76 (1H, s, br.); 8.26 (1H, d); 7.24 (1H, d); 3.76 (3H, s) ppm.

$^{13}$C-NMR 158.2 (s); 154.1 (s, q); 142.5 (s); 137.4 (d); 124.7 (s); 115.8 (s); 112.1 (d); 52.3 (q) ppm.

The invention claimed is:

1. A method for preparing a compound of formula (I) and/or salt thereof,

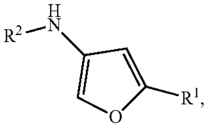

(I)

in which $R^1$ is $CF_3$, $CF_2H$, $CCl_3$, $COOCH_3$, $COOC_2H_5$, and $R^2$ is H, $COCF_3$, $COCH_3$, $COCCl_3$, phenyl-$CH_2$, (diphenyl)CH, $CH_3OCO$, $(CH_3)_3COCO$, comprising converting a compound of formula (II)

(II)

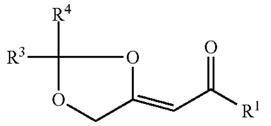

in which $R^3$ and $R^4$ are each independently H and or $CH_3$, and $R^1$ has the definitions specified above, with aid of an amine of formula $R^5$—$NH_2$ (V) to a compound of formula (III)

(III)

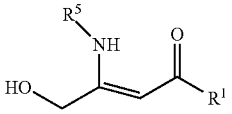

in which $R^5$ is H, and then reacting said compound of formula III in presence of a dehydrating reagent to give a compound of formula (I).

2. The method according to claim 1, wherein definitions of radicals of compounds of formulae (I), (II), (III), and (V) are as follows:

$R^1$ is $CF_3$, $COOCH_3$, or $COOC_2H_5$, $R^2$ is H, $COCF_3$, or $(CH_3)_3COCO$, and $R^3$ and $R^4$ are each $CH_3$.

3. The method according to claim 2, wherein definitions of radicals of compounds of formulae (I), (II), (III), and (V) are as follows:

$R^1$ is $COOCH_3$ or $COOC_2H_5$, and $R^2$ is H.

4. The method according to claim 3, wherein definitions of radicals of compounds of formulae (I), (II), (III), and (V) are as follows:

$R^1$ is $COOCH_3$.

5. The method according to claim 1, wherein the reaction of the compound of formula III is carried out at approximately room temperature.

6. The method according to claim 1, wherein the reaction of the compound of formula III is further in the presence of at least one solvent selected from the group consisting of methanol, ethanol, isopropanol, butanol, acetonitrile, N,N-dimethylacetamide, toluene, and chlorobenzene.

7. The method according to claim 1, wherein the dehydrating reagent comprises at least one compound selected from the group consisting of $SOCl_2$, $POCl_3$, $PCl_3$, phosgene, diphosgene, triphosgene, ClCOCOCl, $(CF_3CO)_2$, $P_4O_{10}$, $SO_2F_2$, and HCL, or comprises a mixture of trimethyl orthoformate and triethyl orthoformate.

8. The method according to claim 7, wherein the dehydrating reagent comprises at least one compound selected from the group consisting of $SOCl_2$, $POCl_3$, $PCl_3$, phosgene, diphosgene, triphosgene, and ClCOCOCl.

9. The method according to claim 8, wherein the dehydrating reagent comprises at least one compound selected from the group consisting of $OCl_2$, $POCl_3$, ClCOCOCl, and phosgene.

10. A method for preparing a compound of formula (I) and/or salt thereof, (I)

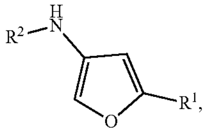

in which $R^1$ is $CF_3$, $CF_2H$, $C_2F_5$, $CF_2Cl$, $CCl_3$, $COO(C_1\text{-}C_4)$alkyl, or COOH, $R^2$ is H, $CH_3CO$, $CCl_3CO$, $CF_3CO$, phenyl-CO, $CH_3OCO$, $(CH_3)_3COCO$, phenyl, phenyl-$CH_2$, or (diphenyl)CH, comprising converting a compound of formula (II)

(II)

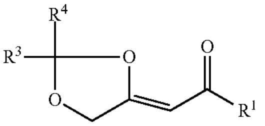

in which $R^3$ and $R^4$ are each independently H or $C_1$-$C_4$-alkyl, and $R^1$ has the definitions specified above, with aid of an amine of formula $R^5$—$NH_2$ (V) to a compound of formula (III)

(III)

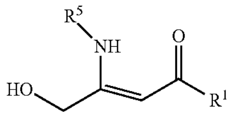

in which $R^5$ is H, phenyl, phenyl-$CH_2$, or (diphenyl)CH, and then reacting said compound of formula III in presence of a dehydrating reagent to give a compound of formula (I), wherein the dehydrating reagent comprises at least one compound selected from the group consisting of $SOCl_2$, $POCl_3$, $PCl_3$, phosgene, diphosgene, triphosgene, ClCOCOCl, $(CF_3CO)_2$, $P_4O_{10}$, $SO_2F_2$, and HCL, or comprises a mixture of trimethyl orthoformate and triethyl orthoformate.

11. The method according to claim 10, wherein definitions of radicals of compounds of formulae (I), (II), (III), and (V) are as follows:

$R^1$ is $CF_3$, $CF_2H$, $CF_2Cl$, $C_2F_5$, $CCl_3$, $COOCH_3$, or $COOC_2H_5$, $R^2$ is H, $CF_3CO$, $CH_3CO$, $CCl_3CO$, phenyl, phenyl-$CH_2$, (diphenyl)CH, $CH_3OCO$, or $(CH_3)_3COCO$, $R^3$ and $R^4$ are each independently H or $CH_3$, and $R^5$ is H, phenyl, phenyl-$CH_2$, or (diphenyl)CH.

12. The method according to claim 11, wherein definitions of radicals of compounds of formulae (I), (II), (III), and (V) are as follows:

$R^1$ is $CF_3$, $CF_2H$, $CCl_3$, $COOCH_3$, or $COOC_2H_5$, $R^2$ is H, $COCF_3$, $COCH_3$, $COCCl_3$, phenyl-$CH_2$, (diphenyl)CH, CHOCO, or $(CH_3)_3COCO$, $R^3$ and $R^4$ are each independently H or $CH_3$, and $R^5$ is H.

13. The method according to claim 12, wherein definitions of radicals of compounds of formulae (I), (II), (III), and (V) are as follows:

$R^1$ is $CF_3$, $COOCH_3$, or $COOC_2H_5$, $R^2$ is H, $COCF_3$, or $(CH_3)_3COCO$, and $R^3$ and $R^4$ are each $CH_3$.

14. The method according to claim 13, wherein definitions of radicals of compounds of formulae (I), (II), (III), and (V) are as follows:

$R^1$ is $COOCH_3$ or $COOC_2H_5$, and $R^2$ is H.

15. The method according to claim 14, wherein definitions of radicals of compounds of formulae (I), (II), (III), and (V) are as follows:

$R^1$ is $COOCH_3$.

16. The method according to claim 10, wherein the reaction is carried out at approximately room temperature.

17. The method according to claim 10, wherein the reaction of the compound of formula III is further in the presence of at least one solvent selected from the group consisting of methanol, ethanol, isopropanol, butanol, acetonitrile, N,N-dimethylacetamide, toluene, and chlorobenzene.

18. The method according to claim 10, wherein the dehydrating reagent comprises at least one compound selected from the group consisting of $SOCl_2$, $POCl_3$, $PCl_3$, phosgene, diphosgene, triphosgene, and ClCOCOCl.

19. The method according to claim 18, wherein the dehydrating reagent comprises at least one compound selected from the group consisting of $SOCl_2$, $POCl_3$, ClCO-COCl, and phosgene.

* * * * *